(12) United States Patent
Bergstrom et al.

(10) Patent No.: US 10,493,380 B2
(45) Date of Patent: Dec. 3, 2019

(54) CHROMATOGRAPHY MEDIUM

(71) Applicant: GE Healthcare BioProcess R&D AB, Uppsala (SE)

(72) Inventors: Jan Bergstrom, Balinge (SE); Gunnar Glad, Uppsala (SE); Bo-Lennart Johansson, Uppsala (SE); Jean-Luc Maloisel, Uppsala (SE); Nils Norrman, Uppsala (SE); Tobias E. Soderman, Uppsala (SE)

(73) Assignee: GE Healthcare BioProcess R&D AB, Uppsala (SE)

( * ) Notice: Subject to any disclaimer, the term of this patent is extended or adjusted under 35 U.S.C. 154(b) by 49 days.

(21) Appl. No.: 15/183,526

(22) Filed: Jun. 15, 2016

(65) Prior Publication Data

US 2017/0050121 A1    Feb. 23, 2017

Related U.S. Application Data

(62) Division of application No. 12/988,707, filed as application No. PCT/SE2009/050406 on Apr. 21, 2009, now abandoned.

(30) Foreign Application Priority Data

Apr. 22, 2008 (SE) ..................... 0800923

(51) Int. Cl.
| | | |
|---|---|---|
| *B01D 15/34* | (2006.01) | |
| *B01D 15/32* | (2006.01) | |
| *B01J 20/28* | (2006.01) | |
| *B01J 20/285* | (2006.01) | |
| *B01J 20/287* | (2006.01) | |
| *B01J 20/32* | (2006.01) | |
| *B01J 39/26* | (2006.01) | |
| *C07K 1/20* | (2006.01) | |
| *C07K 16/00* | (2006.01) | |
| *C12N 7/00* | (2006.01) | |
| *G01N 1/40* | (2006.01) | |

(52) U.S. Cl.
CPC .......... *B01D 15/327* (2013.01); *B01J 20/285* (2013.01); *B01J 20/287* (2013.01); *B01J 20/28009* (2013.01); *B01J 20/3212* (2013.01); *B01J 20/3293* (2013.01); *B01J 39/26* (2013.01); *C07K 1/20* (2013.01); *C07K 16/00* (2013.01); *C12N 7/00* (2013.01); *G01N 1/405* (2013.01); *C12N 2760/16151* (2013.01)

(58) Field of Classification Search
CPC .. A61K 2039/5258; A61K 2039/55516; C07C 211/27; C07C 211/49; G01N 2500/10; G01N 33/54353; G01N 33/545; G01N 33/6845; B01D 15/327; B01D 15/361; B01D 15/362; B01D 2252/20421; C07K 1/18; C07K 7/06; C07K 14/005; C07K 1/16

See application file for complete search history.

(56) References Cited

U.S. PATENT DOCUMENTS

| | | |
|---|---|---|
| 6,531,523 B1 | 3/2003 | Davankov |
| 2003/0125656 A1 | 7/2003 | Davankov et al. |
| 2005/0079984 A1 | 4/2005 | Miles |
| 2005/0181378 A1 | 8/2005 | Harrold et al. |
| 2005/0267295 A1* | 12/2005 | Belew .................. B01D 15/363 530/412 |

FOREIGN PATENT DOCUMENTS

| | | |
|---|---|---|
| EP | 0966488 | 11/2006 |
| EP | 1764152 | 3/2007 |
| JP | 61-287444 | 12/1986 |
| WO | WO1992/000799 | 1/1992 |
| WO | WO1992/018237 | 10/1992 |
| WO | WO1998/39094 | 9/1998 |
| WO | WO2004/020994 A1 | 4/2004 |
| WO | WO2007064281 A1 | 6/2007 |
| WO | WO2007/054548 A2 | 9/2007 |
| WO | WO2009014481 A1 | 1/2009 |
| WO | WO2009/099375 | 8/2009 |
| WO | WO2010/071264 A1 | 6/2010 |

OTHER PUBLICATIONS

Bruker Daltonics. Purification kits MB-HIC. Bruker Daltonics. 2006:1-6.*
Maa et al. Mixed-bed ion-exchange columns for protein high-performance liquid chromatography. J. Chromatogr. 1988;452:331-345.*
Octylamine. HiScreen™ prepacked columns. gelifesciences.com. 2008;1-18.*
EP 09735164.7 Search Report dated Jul. 15, 2013.
Supelco. Discovery DSC-MCAX (Mixed-Mode Cation Exchange) SPE Products. Sigma-Aldricch. 2003.
Bruker Daltonics. Purification Kits MB-HIC. 2006. p. 1-6.
Walton, W.H. Prewett, W.C. (1949) Proc. Phys. Soc. B. 62, 341-350.
Jansson, J.C. and Ryden, L., Protein Purification—Principles, High Resolution Methods and Applications, VCH, Weinheim, 220-221.
EP Office Action issued in corresponding EP Application No. 09735164.7 dated Oct. 24, 2016.

* cited by examiner

*Primary Examiner* — Lynn Y Fan

(74) *Attorney, Agent, or Firm* — Wood IP LLC

(57) ABSTRACT

The present invention is within the field of chromatography. More precisely, it relates to a novel chromatography medium, namely a hydrophobic medium provided with different lids excluding molecules over a certain size due to the porosity of the hydrophobic medium and/or the porosity of the lid. The invention also relates to use of the separation medium for purification of large molecules, which do not enter the separation medium, as well as small molecules, which enter the separation medium and are eluted from there.

11 Claims, 1 Drawing Sheet

Dextran lid media based on SEPHAROSE™ 6 Fast Flow

OH-lid prototypes based on SEPHAROSE™ 20 Fast Flow and Spinning disc media

US 10,493,380 B2

CHROMATOGRAPHY MEDIUM

CROSS-REFERENCE TO RELATED APPLICATIONS

This application is a divisional of U.S. patent application Ser. No. 12/988,707 filed Oct. 20, 2010, which is a filing under 35 U.S.C. § 371 of international patent application number PCT/SE2009/050406, filed Apr. 21, 2009, which claims priority to application number 0800923-5 filed Apr. 22, 2008 in Sweden, the entire contents of which are hereby incorporated by reference.

FIELD OF THE INVENTION

The present invention is within the field of chromatography. More precisely, it relates to a novel chromatography medium, namely a hydrophobic medium provided with different lids excluding molecules over a certain size due to the porosity of the hydrophobic medium and/or the porosity of the lid.

Within biotechnology, the chromatographic methods suggested up to date are based on different modes of interaction with a target. Thus, for example, in ion-exchange chromatography, the functional groups are permanently bonded ionic groups with their counter ions of opposite charge, while in hydrophobic interaction chromatography (HIC), the interaction between the stationary phase and the component to be separated is based on hydrophobicity.

Chromatography based on hydrophobic interaction is generally divided in to two types named HIC and RPC.

HIC refers to hydrophobic interaction chromatography of proteins using very hydrophilic matrixes to which hydrophobic ligands are immobilized to a very low degree in order to avoid denaturation of separated proteins. In order to adsorb proteins to be separated it is necessary to use high concentrations of an inorganic salt in water. Desorption is usually achieved by gradually lowering the ionic strength in an elution step.

RPC refers to chromatography using matrixes usually silica based functionlized to a very high degree with hydrophobic non polar molecules/ligands usually aliphatic carbon chains containing 4 to 18 carbon atoms. Adsorption is normally achieved without the need of added salt. Desorption or elution is most often done by gradually increasing the content of an organic solvent in the elution solution.

RPC media with 18 carbon chains binds proteins strongly. The proteins are also denaturated to different degree during the binding process. In order to elute the proteins it is necessary to use extraordinary conditions. However RPC media with shorter chains (4 Carbons) may be used together with water/acetonitrile based eluents containing additives such as triflouracetic acid for protein separations.

The stationary phase, also known as the separation matrix, comprises a support, which is commonly a plurality of essentially spherical particles, and ligands coupled to the support. In most separation matrices, the support is porous to allow a larger amount of ligand and consequently more bound target compound in each particle. The support is most often a natural or synthetic polymer and the spherical particles may be produced in a number of different ways. Silica and glass beads are also used. Natural polymers often used for this purpose are the polysaccharides dextran and agarose.

For separation of biomolecules, by chromatographic and batch-wise procedures, the porosity of the matrix (beads, monoliths, packed membranes etc) is very important. Advantages of polymeric media are that it is easy to vary pore size over broad ranges and their high chemical stability e.g. tolerance of high pH:values. A general rule, which is accepted throughout the literature, is to use media with large pore sizes for large molecules. Mass transfer in these pores is a result of diffusion processes and not of convection.

In WO2009/099375, a method is described based on the Spinning Disc technology (Walton and Prewett (Walton, W. H.; Prewett, W. C. (1949) *Proc. Phys. Soc. B.* 62, 341-350) to produce agarose beads having a selected porosity to exclude large molecules.

Humanized monoclonal antibodies (mAbs) hold significant promise as biopharmaceuticals. One of the most challenges faced in the purification of mAbs is their separation from host cell proteins (HCPs) in the cell culture media. A wide variety of mAbs isolation technique is available today that include affinity chromatography on Protein A, ion exchange chromatography and hydrophobic interaction chromatography (HIC). All these techniques involve the use of a mobile phase (adsorption buffer) that must be adjusted to accomplish interaction between mAb-molecules and the ligands. For example, in HIC high amounts of salt must be added to the mobile phase and in case of ion exchange chromatography the pH of the mobile phase must be adjusted so the mAbs are oppositely charged compared to the ion exchange ligand. Furthermore, when the mAbs are adsorbed to the ligand the mobile phase must be adjusted to accomplish desorption of the mAbs.

It would be desirable to obtain a chromatographic medium which has a pore size distribution and surface properties that prevents large molecules, such as mAbs, from entering the beads and which internally can adsorb proteins and other peptides or biomolecules independently of buffer conditions. Ion exchangers aimed for separation of biomolecules are able to adsorb most charged biomolecules at low ionic strength but when the ionic strength is increased over a certain level these media loose the ability to adsorb the sample molecules.

SUMMARY OF THE INVENTION

The present invention provides a medium having such a high hydrophobicity in the core entity that proteins can interact or be adsorbed both at very low and high ionic strengths in a broad pH range.

In a first aspect, the invention relates to a separation medium comprising a porous, hydrophobic core entity; and a porous, hydrophilic lid covering the whole exterior of the core entity, wherein the lid only allows molecules under a certain size to penetrate and interact with the internal part of the core entity of the separation medium.

In a preferred embodiment, preferably also the hydrophobic core entity only allows molecules under a certain size to penetrate and interact with the internal part of the core entity of the separation medium.

The porous hydrophilic lid is a porous outer layer or jacket/shell surrounding the core entity.

The separation medium is preferably provided with a highly hydrophobic core in order to bind proteins and other hydrophobic molecules independently of the properties of the sample and of running conditions such as ionic strength and pH, in case of chromatography, or the supernatant, in case of a batch-wise procedure. The separation medium is preferably bead-shaped but may also be a membrane.

The size exclusion property of the medium is determined by the porosity of one or both of its porous constituents. The certain size referred to above is below the size that excludes the target molecules/organism/particles such as cells, cell particles, virus, virus like particles, plasmids, any type of antibodies, lipids, proteins, peptides and nucleic acids. This medium will efficiently separate low size molecules from larger molecules of the type mentioned above.

The hydrophobic core entity may be hydrophobic per se and may be based on a hydrophobic polymer. For example, styren/ethylstyren/DVB, vinylethers and acrylates containing hydrophobic substituents as well as fluoroalkane-containing polymers.

Alternatively, the hydrophobic core entity is hydrophilic per se and is based on a hydrophilic polymer, functionalized with hydrophobic interaction ligands. The hydrophobic interaction ligands may comprise aliphatic hydrocarbons, such as C1-C30 alkyl, preferably C4-C16 alkyl, and/or aromatic hydrocarbons, such as phenyl, antracene, naphtalene. Independent of ligand, the ligand density should always be optimized for adsorption at low ionic strength and in the purpose of obtaining the desired highly hydrophobic nature of the medium. Preferably, the ligand density should be above normal HIC-levels, i.e. >90 μmole/ml core entity.

The hydrophobic core entity allows adsorption of the molecules (with the lowest molecular weight and/or smallest size) in the sample that are able to penetrate the lid at low ionic strength, such as 0-1 M, preferably 0-0.4 M, most preferably 0-0.1 M, and in the pH interval 2-11.

In one embodiment, the core entity comprises further ligands besides said hydrophobic ligands which may be located on and/or associated with the core entity and/or on the hydrophobic ligands. The further ligands may be hydrophobic and may contain a non dominating charged group. Preferably, said further ligands are electrostatic interaction ligands, i.e. a positive and/or a negative charge ligand. For example, these further ligands may be octylamine ligands, provided with a positive charge, which increases the binding of small negatively charged molecules to the core entity. The amount of further added charged ligands should be adjusted so that they do not interfere too much with the hydrophobic interaction to the main hydrophobic ligand.

In a preferred embodiment, the core entity and lid are made of agarose and the hydrophobic ligands are hydrocarbon ligands comprising 4-16 carbons, preferably octyl ligands.

Preferably, the core entity has a pore size preventing molecules over a certain size from entering the pores. Alternatively, or in addition thereto, a polymeric hydrogel e.g. dextran is provided in the lid to fill the pores and thereby further decrease and adjust the pore size to prevent high molecular weight molecules from entering the pores.

In a further embodiment, the hydrophilic lid comprises any type of chromatography ligands that reversibly bind the molecules within the sample with the highest molecular weight(s) and/or largest size(s). Some of the small molecules will probably also bind to the lid but during the elution step they most probably will penetrate the lid and bind to the core.

For certain applications, such as proteomic analysis, magnetic particles may be incorporated into the core entities of the separation medium.

The invention also relates to a separation medium which comprises the lid bead medium described above in mixture with conventional chromatography media, such as HIC, IE or affinity media. Preferably the lid bead medium comprises up to 10% of the total media volume. In a preferred embodiment of this mixed media, the lid bead medium comprises octyl ligands and the chromatography media comprises a cation exchange media. Benefits of this mixed media are increased resolution between large and small molecules.

In a second aspect, the invention relates to use of the separation medium as described above, for adsorbing molecules under a certain size from a sample at low ionic strength at pH 2-11, preferably in one single step. The procedure may be used to purify molecules over or under said size. Thus this aspect involves a method of using the separation medium comprising a step of adsorbing molecules and optional further step(s).

The pore size referred to above varies with, and is determined by, the size of the target molecule in the specific application. This certain size range preferably corresponds to the size range of molecules/organisms/particles selected from cells, cell particles, bacteria, virus, virus like particles, plasmids, antibodies, lipids, proteins, peptides, nucleic acid. The sample may be, for example, a culture supernatant and the high molecular weight molecule may be a monoclonal antibody. The separation medium will be very useful for addition at cell harvest to rapidly remove undesired enzymes, like proteases, peptidases and nucleases, such as trypsin, chymotrypsin, DNase and RNase. The separation medium may be used in chromatographic or batch mode. Any column or batch format may be used. For some applications, such as purification of biopharmaceuticals for clinical phase I and II studies, disposable columns in RTP (ready to process) format are preferred.

In an alternative embodiment, the adsorbed low molecular weight molecules, such as below 60 000 D, may be the desired molecules, such as biomarkers or drug markers, which are eluted, for example by decreased polarity in the eluent, from the core entity and further analysed. Another example is when the target molecule is adsorbed in the core entity but not used for further analysis, such as for lipid removal.

When the target molecule is a large molecule/organism/particle, such as a cell, cell particles, bacteria, virus, virus like particles, plasmids, antibodies, proteins, it may obtained in the flow-through and thus not adsorbed by the medium.

Alternatively the target molecule is a large molecule/organism/particle, such as a cell, cell particles, bacteria, virus, virus like particles, plasmids, antibodies, proteins, which is adsorbed on the lid. The target molecule is then eluted by a technique appropriate for the chosen absorption mode (e.g. ion exchange: salt and/or a pH gradient, IMAC: imidazol gradient, boronate: sugar or pH gradient, HIC: lowering the salt concentration).

The preferred use of the separation medium according to the invention is for purification of monoclonal antibodies. Another preferred use is wherein the target molecule is a molecule or particle <1 000 kD. This embodiment is suitable for purification of virus, such as influenza virus, but also for other large molecules such as IgM antibodies.

BRIEF DESCRIPTION OF THE DRAWINGS

FIG. 1A: SEPHAROSE™ 20 Fast Flow (20% agarose particle) and Spinning disc and FIG. 1B: lid-dextran SEPHAROSE™ 6 Fast Flow. IgG=monoclonal antibodies; P=proteins with molecular weight less than ca 70 000.

DETAILED DESCRIPTION OF THE INVENTION

The present invention relates to a chromatographic medium which has both hydrophilic and hydrophobic regions in the matrix and may be based on a matrix which is hydrophobic per se, or on a hydrophilic matrix with hydrophobic ligands, and is provided with a hydrophilic outer layer. The medium may also be based on a hydrophilic matrix internally functionalized with hydrophobic ligands (e.g. a hydrophobic internal core in a bead).

Example of Synthetic Path Ways:

Hydrophobic per se start material e.g. DVB beads covered by a hydrophilic and porous layer.

Figure 1B:
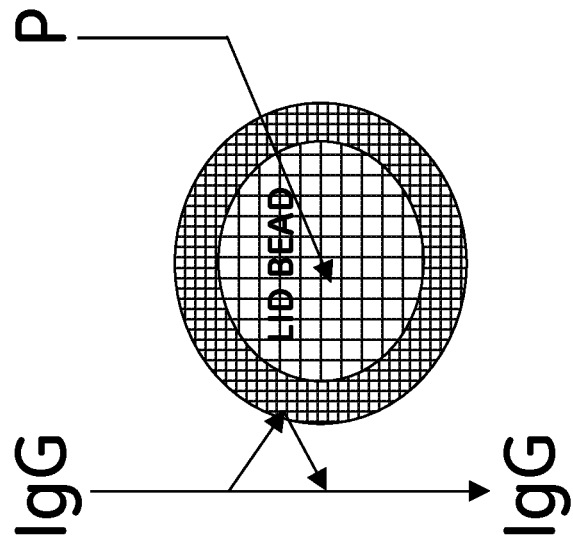
FIGS. 1A and 1B are illustrations of three different bead designs that have been tested.
Figure 1A:
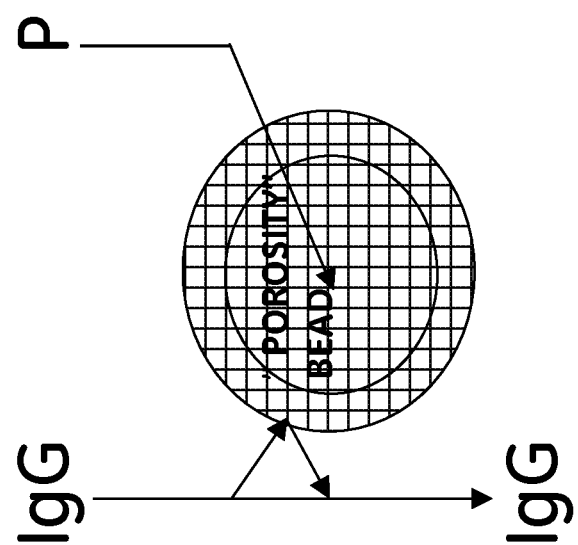

Per se hydrophilic start material fully functionalized with hydrophobic functional groups and then covered by a hydrophilic and porous layer. Layer activation of a hydrophilic matrix and internally couple hydrophobic ligands (FIGS. 1A and 1B).

Layer activation of a hydrophobic matrix and make a hydrophilic functionalization of the outer parts.

The invention also provides a method of separating large molecular weight molecules, such as antibodies, from other components of a liquid, which requires less time and process steps than the prior art methods. This is achieved by a method wherein the liquid comprising the desired high molecular weight molecules, such as antibodies, is contacted with the chromatographic medium, and substantially pure high molecular weight molecules are recovered in non-binding or reversible binding mode. Another advantage is that low molecular weight molecules, such as host cell proteins, adsorb to the internal parts of the medium even at very low ionic strengths.

The support matrix and core entity of the chromatographic medium can be based on organic or inorganic material. It is preferably in the form of an organic polymer, which is insoluble but may be more or less swellable in water. Suitable polymers are polyhydroxy polymers, e.g. based on polysaccharides, such as agarose, dextran, cellulose, starch, pullulan, etc. and completely synthetic polymers, such as polyacrylic amide, polymethacrylic amide, poly (hydroxyalkylvinyl ethers), poly(hydroxyalkylacrylates) and polymethacrylates (e.g. polyglycidylmethacrylate), polyvinylalcohols and polymers based on styrenes and divinylbenzenes, and copolymers in which two or more of the monomers corresponding to the above-mentioned polymers are included. Polymers, which are soluble in water, may be derivatized to become insoluble, e.g. by cross-linking and by coupling to an insoluble body via adsorption or covalent binding. Hydrophobic groups can be introduced on hydrophobic polymers (e.g. on copolymers of monovinyl and divinylbenzenes) by graft polymerization of monomers exhibiting groups which can be converted to OH, or by hydrophilization of the final polymer, e.g. by binding or adsorption of suitable compounds, such as hydrophilic polymers and other hydrophilic compounds. Reactions including epoxides or reactive halogenids may be used.

Suitable inorganic materials to be used in support matrices are silica, glass, zirconium oxide, graphite, tantalum oxide etc.

Preferred support matrices lack groups that are unstable against hydrolysis, such as silanol, ester, amide groups and groups present in silica as such.

In a particularly interesting embodiment of the present invention, the support matrix is in the form of irregular or spherical particles with sizes in the range of 1-1000 µm, preferably 5-50 µm for high performance applications and 50-300 µm for preparative purposes.

An interesting form of support matrix has densities higher or lower than the liquid sample or buffer solutions to be used, such as fermentation feeds. This kind of matrices is especially applicable in large-scale operations for fluidised or expanded bed chromatography as well as for different batch wise procedures, e.g. in stirred tanks. Fluidised and expanded bed procedures are described in WO 92/18237 and WO 92/00799. The most practical use of these matrices has been to combine particles/beads with a density higher than the density of a fluidising liquid with an upward flow. This kind of support matrices in expanded bed mode is particularly beneficial in case the sample solution contains particulate and sticky materials.

The term hydrophilic support matrix in practice means that the accessible surface of the matrix is hydrophilic and protein friendly, i.e. that the surface not irreversibly adsorbs and denaturates proteins. Typically the accessible surfaces on a hydrophilic base matrix expose a plurality of polar groups for instance comprising oxygen and/or nitrogen atoms. Examples of such polar groups are hydroxyl, amino, carboxy, sulphonate (S and SP ligands) ester, ether of lower alkyls (such as (—CH$_2$CH$_2$O—)$_n$H where n is an integer 2, 3, 4 and higher).

A hydrophilic surface coat, possible in the form of hydrophilic extenders belongs conceptually to the support matrix.

In ordinary/established HIC media an increase in polarity by addition of salts to the mobile phase is required to accomplish binding of proteins. The bound proteins are subsequently released from the matrix by lowering the concentration of salt. Thus, a disadvantage of this procedure is the necessity to add salt to the raw material, as this may cause problems and a consequently increased cost to the large-scale user. Adsorption of proteins to ordinary HIC-media is usually performed with a salt concentration between 0.75 and 4 M (Jansson, J.-C. and Rydén, L., Protein Purification—Principles, High Resolution Methods and Applications, VCH, Weinheim, pp. 220-221).

This invention relates to a medium which maximizes the interaction with molecules small enough to penetrate into the hydrophobic core of the separation matrix, such as HCPs, and minimizes the interaction with the largest proteins in the samples, such as MAb-molecules and MAb-dimers in a MAb purification process. Furthermore, one embodiment of the invention enables that mobile phases with no extra addition of salt can be used and that no elution buffer (desorption buffer) is needed to recover the desired high molecular weight molecules or organisms for embodiments with neutral or almost neutral lids (non-binding lids).

Three different approaches for the design of beads aimed for capture of host cell proteins but not large monoclonal antibodies have been tested. In one approach agarose beads based on high contents of agarose (20%) was designed to obtain a bead with a porosity that excludes large proteins (monoclonal antibodies) (FIG. 1A). In a further approach, a prototype based on SEPHAROSE™ 6 Fast Flow and a gel filtration lid was produced. The lid was obtained by coupling dextran to the outer segment of the beads. The pore sizes obtained in the dextran filled segment is designed to prevent large molecules, such as mAbs, to enter the core of the beads (FIG. 1 B). The third approach is based on the spinning disc media described in WO2009/099375. Also in this case the beads were designed to exclude large proteins (FIG. 1 A) by the introduction of a neutral outer segment achieved as described by commonly owned layer activation patents EP 0 966 488 B1 (Process for introducing a functionality.)

During the attachment of the hydrophobic ligands to the different prototypes a synthesis procedure was used to prevent ligands to be coupled to the surface of the beads and in that way also eliminate adsorption due to hydrophobic interaction of monoclonal antibodies to the outer part of the beads. The prototypes are named lid-OH core-octyl media meaning that the octyl ligands only are attached in the core of the beads. Furthermore, the amount of ligands in the core of the beads is adjusted so that host cell proteins are adsorbed using adsorption buffers with very low ionic strengths adjusted to any pH relevant for chromatography of biomolecules.

EXAMPLES

The present examples are presented herein for illustrative purpose only, and should not be constructed to limit the invention as defined by the appended claims.

Example 1: Preparation of Octyl Media Based on SEPHAROSE™ 20 Fast Flow (A), SEPHAROSE™ 6 Fast Flow (B), and Spinning Disc Media (C)

Volumes of matrix refer to settled bed volume and weights of matrix given in gram refer to suction dry weight. For large scale reaction stirring is referring to a suspended, motor-driven stirrer since the use of magnet bar stirrer is prompt to damage the beads. Small-scale reactions (up to 20 mL of gel) were performed in closed vials and stirring refers to the use of a shaking table.

Conventional methods were used for the analysis of the functionality and the determination of the degree of ally-lation, epoxidation, or the degree of substitution of ion exchanger groups on the beads.

A: Preparation of lid-OH core-octyl SEPHAROSE™ 20 Fast Flow

A1: Preparation of SEPHAROSE™ 20 Fast Flow

Agarose (50 g) was dissolved in water (250 g) by heating at 95° C. for approximately 10 hours. The solution was added to toluene (375 mL) and ethyl cellulose (35 g) in an emulsification vessel, the temperature was kept at 70° C. The emulsification vessel was equipped with a blade stirrer. The speed of the stirrer was increased step by step from 150 rpm to 340 rpm, maintaining the temperature at 70° C. When the agarose particles were judged by a microscope to have a desired size the speed was decreased to 150 rpm. Thereafter the emulsion was cooled and the beads were allowed to gel. The beads were washed with ethanol and water.

Water was added to 250 mL beads to a total weight of 310 g. To this suspension 38 g $Na_2SO_4$, 3.0 mL 50% NaOH and 0.25 g $NaBH_4$ was added and the temperature was increased to 47° C. Epichlorohydrine (31.4 mL) and sodium hydroxide solution (21.6 mL) were then added with pumps during 6 h. After the addition was completed the reaction continues over night at 47° C. The slurry was then cooled and neutralized to pH 5-6 with 60% acetic acid. Finally the gel was carefully washed on a glass filter with distilled water. The beads were thereafter sieved on 43 µm and 166 µm cloths.

A2: Preparation of an OH-Lid Allyl SEPHAROSE™ 20 Fast Flow

Allyl Activated SEPHAROSE™ 20 Fast Flow.

50 g of drained SEPHAROSE™ 20 Fast Flow (SEPHAROSE™ 6 Fast Flow, GE Healthcare, Uppsala, Sweden) was mixed with 15 mL of 50% NaOH solution, 6 g of $Na_2SO_4$ and 0.1 g of $NaBH_4$. The mixture was stirred at 50° C. for 1 h, followed by addition of 30 mL allyl glycidyl ether (AGE). The reaction slurry was stirred at 50° C. for 17 h. Then the gel was washed on a glass filter with distilled water, ethanol and finally with distilled water again.

Partial Bromination and NaOH Treatment (Preparation of OH-Lid).

10 mL of drained allylated SEPHAROSE™ 20 Fast Flow, was stirred in 5 mL of distilled water and 0.4 g sodium acetate. 125 µL of bromine, dissolved in a capped vial with 10 mL distilled water was added and the stirring was continued for 5 minutes. After washing with water, the drained gel was stirred with 7.5 mL of 2 M NaOH at 50° C. for 18 h, followed by washing with water. Remaining allyl content in the core of the beads was measured by titration; 0.37 mmol/mL.

A3: Core Coupling

Coupling of Octyl in the Core of the Beads.

4.5 mL of OH-lid SEPHAROSE™ 20 Fast Flow (see above), is fully brominated and washed. Drained gel was mixed with a solution of 1.25 mL octanethiol in 4.5 mL 2 M NaOH and 1 mL of ethanol, followed by stirring at 50° C. for 16 h. After washing with water, ethanol and water, the gel was stored in 20% ethanol.

B: Preparation of Lid-Dextran Core-Octyl SEPHAROSE™ 6 Fast Flow

B1: Preparation of a Lid-Dextran Allyl SEPHAROSE™ 6 Fast Flow

Allylation of SEPHAROSE™ 6 Fast Flow.

SEPHAROSE™ 6 Fast Flow was allylated according to above and the allyl content was determined by titration to 259 µmol/mL.

Partial Bromination.

Allylated SEPHAROSE™ 6 Fast Flow (100 mL) was weighed into a flask and 900 mL of distilled water and 1.3 g sodium sulphate was added. 0.3 equivalents of bromine, 400 µL, were then added with a pipette during vigorous stirring. After approximately 5 minutes (when the bromine was consumed) the gel was washed with distilled water on a glass filter.

Dextran Coupling.

51 mL of the partially brominated gel was transferred to a flask, and a solution of 30 g Dextran AB in 125 mL of distilled water was added. After stirring for 30 minutes, 10 g of NaOH and 0.5 g $NaBH_4$ were added and the slurry was heated to 50° C. and left stirring over night. After approximately 18 hours the pH was adjusted to approximately 7 with acetic acid (60% solution). The gel was then washed with distilled water on a glass filter.

B2: Core Coupling

Coupling of Octyl in the Core of the Beads.

10 mL of drained gel (Dextran coupled SEPHAROSE™ 6 Fast Flow, see above) were put with distilled water into a beaker and vigorous overhead stirring was begun. Bromine was added until the slurry had a remaining deeply orange/yellow colour. After 10 minutes of stirring sodium formate (approximately 1.5 g) was added until the slurry was completely discoloured. The gel was then washed with distilled water on a glass filter. Drained brominated gel was weighed into a flask and 10 mL of distilled water and 2.3 mL of octanethiol was added. The pH was then adjusted to approximately 12.5 with NaOH (50%-solution). The mixture was then left stirring in 50° C. over night. After 20 hours the gel was washed with distilled water and ethanol.

C: Preparation of Lid-OH Core-Octyl Spinning Disc Medium

C1: Preparation of Spinning Disc Medium

6% agarose solutions were used as starting material. Temperature, cooling rate, viscosity, speed and agarose flow rate (to the disc) were investigated with respect to the porosity response.

The Spinning Disc apparatus was manufactured by ABB Industriservice according to given specification (see below):
Steel quality: SS 2343-02 (for all specified items)
Polymeric materials: PTFE, polycarbonate (dome protection), EPDM (Ethylene Propylene Diene Monomer), silicon rubber.
Dome height: 900 mm
Capture basin diameter: 2400 mm including water drain channel
Capture basin slope: 3°
Number of discs: 6
Disc diameter: 200 mm
General disc thickness: maximum 5.2 mm
Disc thickness at edges: 12.4 mm including 135° slope
Upper pressure compensation chamber diameter (for liquid agarose solution): 73 mm
Upper pressure compensation chamber height: 6 mm
Number of distribution needles: 6
Inner diameter of needles: 0.7 mm The agarose solution was fed to six discs via needles. By using six discs instead of one, there is an increase in capacity. The agarose flow was the same to each of the six discs. This means that the bead size originating from each disc is the same. The speed range of the discs was adjusted within 3001-3010 rpm and the relative humidity in the dome was 100%. If the relative humidity is less than 100% there is a risk that water will be evaporated from the agarose drops.

Allylated, 6% agarose solutions adjusted to 69.7° C. and a viscosity within 397-421 mPas were used to feed the spinning discs. The flow rate of the agarose solution to the discs was adjusted to 170 mL/min. The capture water temperature was 20.1° C.

The porosity of the spinning disc beads after cross-linking with epichlorohydrin is presented in Table 1. The porosity was estimated with different dextrans and the void volume was obtained with blue dextran 2000. The spinning disc prototype was produced to obtain a porosity that not allows immunoglobulins to penetrate the beads. This means that molecules with a molecular weight larger than ca. 150 000 g/mol should not diffuse into the beads.

TABLE 1

The $K_{av}$-value of five different dextran standards for the spinning disc prototype

| Mw Dx | $K_{av}$ |
|---|---|
| 9890 | 0.655 |
| 43500 | 0.382 |
| 66700 | 0.276 |
| 123600 | 0.021 |
| 196300 | 0.013 |

[1]The $K_{av}$-value vas calculated as: $(V_R - V_O)/(V_C - V_O)$ where $V_R$ = retention volume of dextran standards, $V_O$ = void volume and $V_C$ = geometric volume of the column.

The particle size was 190 µm±5 µm. The spinning disc prototype was used to produce media for capture of proteins with a molecular weight less than approximately 70 000 g/mol while larger molecules such as immunoglobulins (human IgG) should not be able to diffuse into the beads and interact with the ligands in the core of the beads.

C2: Preparation of an OH-Lid-Allyl Spinning Disc Medium

Allyl Activated Spinning Disc Medium.

Spinning disc medium was washed with distilled water on a glass filter. The gel, 25 mL, was drained on the filter and weighed into a 3-necked round bottomed flask. NaOH (20 mL, 50%-solution) was added and mechanical stirring started. Sodium borohydride, 0.1 g, and sodium sulphate, 2.9 g, were added to the flask and the slurry heated to 50° C. on a water bath. After approximately one hour 27.5 mL of allyl glycidyl ether was added. The slurry was then left under vigorously stirring over night. After about 20 hours the slurry was transferred to a glass filter and the pH adjusted to around 7 with acetic acid (60%). The gel was then washed with distilled water (×4), ethanol (×4) and distilled water (×4). The allyl content was then determined by titration to 321 µmol/mL.

Partial Bromination and NaOH Treatment (Preparation of OH-Lid).

Allylated gel, 11.6 mL, was weighed into a flask and 90 mL of distilled water and 1 g sodium sulphate was added. 0.3 equivalents of bromine, 57 µL, were then added with a pipette during vigorous stirring. After approximately 5 minutes (when the bromine was consumed) the gel was washed with distilled water on a glass filter. 5 mL of the partially brominated gel was transferred to a flask with water solution. NaOH (50%-solution) was then added to pH>13 and the slurry were heated to 50° C. and left stirring over night. After approximately 18 hours the pH was adjusted to approximately 7 with acetic acid (60% solution). The gel was then washed with distilled water on a glass filter.

C3: Core Coupling

Coupling of Octyl in the Core of the Beads.

5 mL of drained OH-lid spinning disc medium was put with distilled water into a beaker and vigorous overhead stirring was begun. Bromine was added until the slurry had a remaining deeply orange/yellow colour. After 10 minutes of stirring sodium formate (approximately 1.5 g) was added until the slurry was completely discoloured. The gel was then washed with distilled water on a glass filter.

Drained brominated gel was weighed into a flask and 10 mL of distilled water and 2 mL of octanethiol was added. The pH was then adjusted to approximately 12.5 with NaOH (50%-solution). The mixture was then left stirring in 50° C. over night. After 20 hours the gel was washed with distilled water and ethanol.

Example 2: Chromatographic Evaluation of the Three Prototypes Based on Octyl Ligands in the Core of the Beads The three different octyl media to be investigated (Prototypes: lid-OH core-octyl SEPHAROSE™ 20 Fast Flow, lid-OH core-octyl spinning disc and lid-dextran octyl core SEPHAROSE™ Fast Flow), with respect to breakthrough capacity, were packed in HR 5/5 columns and the sample solution was pumped at a flow rate of 0.3 or 1.0 mL/min through the column after equilibration with buffer solution. The breakthrough capacity was evaluated at 10% of the maximum UV detector signal (280 nm). The maximum UV signal was estimated by pumping the test solution directly into the detector. The breakthrough capacity at 10% of absorbance maximum ($Q_{b10\%}$) was calculated according to the formula:

$$Q_{b10\%} = (T_{R10\%} - T_{RD}) \times C/V_c$$

where $T_{R10\%}$ is the retention time (min) at 10% of absorbance maximum, $T_{RD}$ the void volume time in the system (min), C the concentration of the sample (4 mg protein/mL) and $V_c$ the column volume (mL). The adsorption buffer used at breakthrough capacity measurements was 25 mM TRIS (pH 8.0) or 50 mM acetate (pH 4.75).

Prototype lid-OH core-octyl SEPHAROSE™ 20 Fast Flow was also tested with a clarified feed in flow-through mode. The feed (32 mL) was pumped through a HR 5/5 column packed with the prototype and the flow-through fraction (36 mL) was analysed with respect to the amount of host cell proteins (HCP) and the amount of monoclonal antibody recovered. The adsorption buffer used at these experiments was 25 mM phosphate buffer adjusted to pH 7.2.

A: Sample

The samples used for breakthrough measurements were human immunoglobulin (IgG, Gammanorm), ovalbumin and lysozyme. The proteins were dissolved in the adsorption buffers at a concentration of 4 mg/mL and only one protein at a time was applied into the column.

The monoclonal antibody (mAb) was an IgG1 (based on IEF its pI is in the range 7.5 to 8.4), expressed in NS0 cells. The filtered non-purified cell culture supernatant was used as sample. The concentration of the mAb in the sample was 1.3 mg/mL and 32 mL of the sample were applied to the column (HR 5/5 column packed with prototype lid-OH core-octyl SEPHAROSE™ 20 Fast Flow). The growth medium used at production of the monoclonal antibody was DMEM (Gibco) and 10% fetal calf serum (FCS, Gibco).

B: Instrumental

Apparatus

LC System: ÄKTAexplorer 10 XT or equal
Software: UNICORN™
Column: HR 5/5
Instrument Parameters
Flow rate: 0.3, 0.5 or 1.0 mL/min
Detector cell: 10 mm
Wavelength: 280 nm B1: UNICORN™ Method The main method used at breakthrough experiments is depicted below:

0.00 Base CV 1.00 {mL} #Column volume {mL} Any
0.00 Block Start Conditions
   0.00 Base SameAsMain
   0.00 Wave length 280 {nm} 254 {nm} 215 {nm}
   0.00 AvaragingTime 2.56 {sec}
   0.00 Alarm Pressure Enable 3.00 {MPa} 0.00 {MPa}
   0.00 End Block
0.00 Block Column Position
0.00 Block Equilibration
   0.00 Base SameAsMain
   0.00 PumpAInlet A1
   0.00 BufferValveA1 A11
   0.00 Flow 0.3 {mL/min}
   1.00 Set Mark ( )#column name
   3.9 AutoZeroUV
   5.0 #Equilibration volume End Block
0.00 Block Sample Loading
   0.00 Base volume
   0.00 Flow (1)#flow rate {mL/min}
   0.00 Set Mark ( )#sample
   0.00 InjectionValve Inject
   0.00 Watch UV Greater Than (100) #20 percent maxabs {mAu} END BLOCK
   49.00 InjectionValve Load
   49.00 End Block
0.00 Block Column Wash
   0.00 Base SameAsMain
   0.00 InjectionValve Load
   0.00 Watch Off UV
   0.00 PumpAInlet A1
   0.00 BufferValveA1 A11
   0.00 Watch UV Less Than (20) #5 percent {mAu} END BLOCK
   20.00 End Block
0.00 Block Gradient Elution
   0.00 Base SameAsMain
   0.00 PumpBInlet B1
   0.00 Gradient 100 {% B} 2.00 {base}
   0.00 Flow 0.30 {mL/min}
   10.00 Gradient 0.00 {% B} 0.00 {base}
   10.00 End Block
0 Block Reequilibration
   0.00 End Method C: Host Cell Protein (HCP) Analysis Samples for ELISA were pre-treated by addition of 10% 2.0 M Tris, 1% BSA, 0.5% TWEEN™ 20, pH 8.0 (50 µL BSA solution to 450 µL sample). The samples were diluted in "Sample Diluent Buffer" (catalogue number F223A, Cygnus Technologies) and analyzed by a NS/0 HCP ELISA kit (catalogue number F220, Cygnus Technologies) using the "High sensitivity protocol" specified in the kit. The spectrophotometer VERSAMAX™ and the software SOFTMAX® Pro, both from Molecular Devices, was used for reading and evaluation of the plates.

D: Results

D1: Lid-OH Core-Octyl SEPHAROSE™ 20 Fast Flow

Lid-OH core-octyl SEPHAROSE™ 20 Fast Flow is based on SEPHAROSE™ 20 Fast Flow with octyl as core ligand. The base matrix SEPHAROSE™ 20 Fast Flow is designed with high content of agarose in order to obtain a porosity that prevents monoclonal antibodies to penetrate the beads. In this case SEPHAROSE™ 20 Fast Flow was activated with a high degree of allyl groups (0.37 mmol/mL) meaning that high ligand content was obtained in the core of the beads.

The breakthrough capacity of Lysozyme and IgG of the prototype based on SEPHAROSE™ 20 Fast Flow (Lid-OH core-octyl SEPHAROSE™ 20 Fast Flow) was tested. As adsorption buffer 25 mM TRIS (pH=8.0) was used and 1.0 M NaOH+30% isopropanol was used as desorption buffer and the flow rate was adjusted to 1.0 mL/min. The prototypes were packed in HR 5/5 columns.

As a result of the test, IgG was not adsorbed ($Q_{b10}$=0) while lysozyme had a breakthrough capacity ($Q_{b10}$) of about 10 mg/mL. It can be noted that these results were obtained with 25 mM TRIS (pH=8.0) as mobile phase and therefore clearly shows that no extra salt addition is necessary to accomplish adsorption of small proteins.

This type of media is mainly aimed to be used for only one cycle. However it is possible to elute adsorbed host cell proteins. To verify this adsorbed lysozyme was eluted by using 1.0 M NaOH+30% isopropanol as desorption buffer.

D2: Lid-Dextran Core-Octyl SEPHAROSE™ 6 Fast Flow

This prototype is based on SEPHAROSE™ 6 Fast Flow that has a porosity that makes it possible for IgG to diffuse into the matrix. Therefore, according to FIG. 1B the pore sizes in the outer part of the beads have been reduced by attaching dextran and in that way prevent IgG to diffuse into the beads. According to Table 2 the breakthrough capacity of IgG was 0 mg/mL which clearly proves that IgG not diffuse into the beads. However, a relatively high breakthrough capacity was observed for ovalbumin (16 mg/mL). The molecular weight of ovalbumin and IgG is approximately 43 000 and 150 000 g/mol, respectively. This means that the dextran lid has a high "size-selectivity" and can allow ovalbumin to diffuse into the beads while IgG is prevented to interact with the core ligands.

TABLE 2

Breakthrough capacity ($Q_{b10}$) of IgG and ovalbumin for two different prototypes packed in HR 5/5 columns.

| Prototype | $Q_{b10}$ IgG[1] (mg/mL) | $Q_{b10}$ Ovalbumin[1] (mg/mL) |
|---|---|---|
| Lid-dextran octyl-core SEPHAROSE™ 6 Fast Flow | 0 | 16 |
| Lid-OH octyl-core spinning disc | 0.6 | 14 |

[1]As adsorption buffer was 50 mM acetate buffer (pH = 4.75) used and 1.0M NaOH + 30% isopropanol was used as desorption buffer and the flow rate was adjusted to 1.0 mL/min.

D3: Lid-OH Core-Octyl Spinning Disc

Breakthrough Measurements.

Lid-OH core-octyl Spinning disc is based on a Spinning disc beads with octyl as core ligand. The Spinning disc medium was designed to obtain a porosity that prevents monoclonal antibodies to penetrate the beads. The spinning disc prototype was activated with a high degree of allyl groups (0.32 mmol/mL) meaning that high ligand content was obtained in the core of the beads. Furthermore, no ligands were coupled in the outer part of the beads (see the preparation of the beads). According to Table 1 the IgG breakthrough capacity was very low (0.6 mg/mL) while the capacity of ovalbumin was 23 times higher. These results also show that the porosity of the spinning disc prototype means that very small amounts of IgG are able to diffuse into the core of the beads.

MAb Feed Application.

Clarified feed that had not been run on any other chromatography column was applied to an HR 5/5 column packed with prototype lid-OH core-octyl spinning disc. The column was run in flow-through mode and the flow-through fraction was sampled and analysed with respect of the recovery of the mAb and the amount of host cell proteins (HCP).

32 mL of mAb (1.3 mg mAb/mL) was applied to a HR 5/5 column packed with the prototype lid-OH core-octyl spinning disc. As adsorption buffer was 25 mM Na-phosphate (pH=7.2) used and 1.0 M NaOH+30% isopropanol was used as desorption buffer. The flow-rate was adjusted to 0.5 mL/min and 36 mL of the flow-through fraction was sampled.

In Table 3 are the results from recovery and HCP measurements presented. The HCP content was reduced by more than 50% and the recovery of the mAb was 89%.

TABLE 3

Yield and HCP reduction obtained in the experiment described in Example 3.

| Sample | Yield (%) | HCP (µg/mL) |
|---|---|---|
| Start material | 100 | 791 |
| Flow-through fraction[1] | 89 | 341 |

[1]36 mL were sampled (flow-through fraction) and 32 mL of the mAb solution were applied to the column (see the experimental section).

Example 3: Purification of Influenza Virus

When producing influenza virus at large scale aiming at influenza vaccines it is important to reduce the levels of protein and DNA in the final preparation.

The particles of the present invention are well suited for the purification of viruses since viral particles are significantly larger in size than most of the contaminants. This is illustrated in the following example.

Analysis Methods

Virus Concentration

The DotBlot HA assay was used according to a standard protocol.

DNA Concentration

The PICOGREEN® DNA assay was used according to the manufacturers instruction (available from Invitrogen).

Protein Concentration

The Bradford protein assay was used according to the manufacturers instruction (available from Bio-Rad)

Agarose Gel Electrophoresis for Analysis of Molecular Weight Distribution in DNA Sample.

An E-GEL® Agarose Gel 0.8% (Invitrogen) precast gel was used according to the manufacturers instructions The DNA ladder used was 1 kb Plus DNA marker (Invitrogen)

Sample

An influenza virus sample produced in-house was used in the study. The virus was propagated in MDCK cells until lysis occurred. Influenza virus strain A/H1N1/Solomon Islands was used. After lysis, the material was concentrated ~10× in an ultrafiltration (UF) step and another ~2× in a diafiltration (DF) step (Hollow Fiber Cartridge 500 kDa). The diafiltration buffer was 50 mM Tris-HCl, 150 mM NaCl pH 7.3 and the sample was frozen until used.

Chromatography Method and Results

Column: 2 mL TRICORN™ 5/100 column packed with particles of the present invention with 7 µm thick neutral outer layer and octyl amine as ligand in the interior. The particles in this example are agarose particles.

10 mL of influenza virus sample was applied at a flow rate of 75 cm/h. The flow-through fraction was collected.

The starting material and flow-through fraction was analysed for virus concentration, DNA concentration and protein concentration. The virus recovery, DNA depletion and protein depletion was calculated. The results are shown in Table 4 and Table 5.

TABLE 4

Analysis results

| Sample | Amount of virus [µg HA] | Amount of DNA [µg] | Amount of protein [µg] |
|---|---|---|---|
| Start Material | 600 | 555 | 4300 |
| Flow-through fraction | 582 | 233 | 780 |

TABLE 5

Virus recovery, protein and DNA depletion

| Virus recovery [%] | DNA depletion [%] | Protein depletion [%] |
|---|---|---|
| 97 | 42 | 80 |

The results show that good protein depletion is obtained which is the main function of this purification step. The DNA depletion is lower, and this can be explained by the presence of high molecular weight DNA in this particular sample.

DNA with molecular weight up to around 500 base pairs are efficiently removed while the larger DNA cannot enter the pore structure and bind to the positively charged octyl amine ligands situated in the inner part of the particles.

A second purification step such as a conventional anion exchange step could remove the larger DNA in this case.

Alternatively the sample can be treated with a nuclease such as BENZONASE® to reduce the molecular weight to well below 500 base pairs and in that way obtain almost complete DNA and protein depletion when the influenza virus sample is passed through a column packed with particles of the present invention.

The invention claimed is:

1. A method for separating at least one target substance from a sample,
the method comprising,
applying a sample comprising at least one target substance onto an agarose based separation medium, wherein the at least one target substance is selected from a virus and an antibody and wherein said separation medium comprises a porous core entity functionalized with hydrophobic octylamine ligands having a ligand density of greater than 90 µmole/mL, and a porous hydrophilic lid covering the core entity,
allowing molecules having a size of <60,000 D from the sample to penetrate the hydrophilic lid and absorb onto-the hydrophobic octylamine ligands of said core entity of the separation medium to remove these molecules from the sample, and
obtaining said target substance in a flow-through fraction of the sample.

2. The method of claim 1, wherein said separation medium is mixed with a cation exchange chromatography media and said separation medium comprises up to 10% of the total volume of the combined separation medium and the chromatography media.

3. The method of claim 1, wherein the sample comprises at least one of DNA and proteins which absorb onto said hydrophobic octylamine ligands in the core entity of the separation medium and are separated from said target substance in the flow-through fraction of the sample.

4. The method of claim 1, wherein the sample comprises host cell proteins which absorb onto said hydrophobic octylamine ligands in the core entity of the separation medium and are separated from said target substance in the flow-through fraction of the sample.

5. The method of claim 1, further comprising providing a hydrogel to said lid, wherein said hydrogel fills pores within said lid, thereby further decreasing and adjusting the size of said pores to prevent high molecular weight target substance from entering said pores.

6. The method of claim 1, wherein magnetic particles are incorporated into said core entity.

7. The method of claim 1, wherein said hydrophobic ligands further comprise electrostatic interaction functionality.

8. A method for separating a virus from a sample that comprises the virus and at least one of DNA and proteins, the method comprising,
applying the sample onto an agarose-based separation medium, wherein said separation medium comprises a porous core entity functionalized with hydrophobic octylamine ligands having a ligand density of greater than 90 µmole/mL and a porous hydrophilic lid covering the core entity and,
allowing the at least one of DNA and proteins from the sample to penetrate the hydrophilic lid and absorb onto the hydrophobic octylamine ligands of said core entity of the separation medium to remove the at least one of DNA and proteins from the sample, and
obtaining said virus in a flow-through fraction of the sample.

9. The method of claim 8, wherein said separation medium is mixed with a cation exchange chromatography media and said separation medium comprises up to 10% of the total volume of the combined separation medium and the chromatography media.

10. The method of claim 8, further comprising providing a hydrogel to said lid, wherein said hydrogel fills pores within said lid, thereby further decreasing and adjusting the size of said pores to prevent high molecular weight target substance from entering said pores.

11. The method of claim 8, wherein magnetic particles are incorporated into said core entity.

* * * * *